(12) United States Patent
Stiene et al.

(10) Patent No.: US 7,005,857 B2
(45) Date of Patent: Feb. 28, 2006

(54) DEVICE FOR MEASURING BLOOD COAGULATION AND METHOD THEREOF

(75) Inventors: Matthias Stiene, Scotland (GB); Tanja Richter, Scotland (GB); Jerome McAleer, Wantage (GB); Elliot Plotkin, Scotland (GB); Manuel Alvarez-Icaza, Scotland (GB); John Allen, Mendota Heights, MN (US)

(73) Assignee: Lifescan Scotland Limited, Inverness (GB)

(*) Notice: Subject to any disclaimer, the term of this patent is extended or adjusted under 35 U.S.C. 154(b) by 0 days.

(21) Appl. No.: 10/432,276

(22) PCT Filed: Dec. 19, 2001

(86) PCT No.: PCT/GB01/05644

§ 371 (c)(1),
(2), (4) Date: Oct. 14, 2003

(87) PCT Pub. No.: WO02/50534

PCT Pub. Date: Jun. 27, 2002

(65) Prior Publication Data

US 2004/0072357 A1     Apr. 15, 2004

(30) Foreign Application Priority Data

Dec. 19, 2000  (GB) .................................... 0030929

(51) Int. Cl.
*G01N 27/02* (2006.01)
*G01R 27/08* (2006.01)

(52) U.S. Cl. ........................................ 324/449; 324/722

(58) Field of Classification Search ........ 324/443–450, 324/663–666, 693–696, 722; 422/73; 436/163
See application file for complete search history.

(56) References Cited

U.S. PATENT DOCUMENTS

| 3,699,437 A | 10/1972 | Amram ........................ 324/722 |
| 5,300,779 A * | 4/1994 | Hillman et al. ........... 250/341.1 |
| 5,534,226 A * | 7/1996 | Gavin et al. .................. 422/73 |

FOREIGN PATENT DOCUMENTS

| CA | 2347376 A1 | 4/2000 |
| WO | WO 96/47907 | 9/1999 |

\* cited by examiner

*Primary Examiner*—Vincent Q. Nguyen

(57) ABSTRACT

A device and method for measuring clotting times in a fluid, typically blood, within a microchannel, with the onset of clotting being determined by measurement of the rate of change, or the value, of capacitance or impedance between two electrodes situated on either side of the microchannel. The device includes an upper support member and a lower support member with a microchannel formed therein. The device also includes electrodes situated along the length of the microchannel.

14 Claims, 6 Drawing Sheets

DEVICE FOR MEASURING BLOOD COAGULATION AND METHOD THEREOF

This application claims the benefit of PCT Application No. PCT/GB01/05644 filed Dec. 19, 2001, which claims priority from Great Britain Application No. GB0030929.4 filed Dec. 19, 2000.

FIELD OF INVENTION

The present invention relates to a device and method for measuring the coagulation factors of a biological sample. More specifically, the invention relates to a disposable test-strip to be inserted into a hand-held or portable meter which is able to display the results of the coagulation assay. Such a device is suitable for home-testing or point of care.

BACKGROUND OF THE INVENTION,

The ability of the body to arrest the flow of blood following vascular injury is paramount to continued survival. The process by which this occurs is termed haemostasis and is accomplished by the process of blood coagulation leading to formation of a blood clot or thrombosis. A blood clot consists of a plug of platelets enmeshed in a network of insoluble fibrin particles. Whilst formation of the clot is essential, the persistence of such clots would be dangerous to the body. Thus, in order to minimize damage to the body after the clotting process has served its purpose, healthy cells surrounding the clot release plasmin to digest fibrin, therefore dissolving the clot. However, thrombosis is one of the leading causes of death worldwide due to the flow of blood to vital organs and tissues being blocked by blood clots. Thrombosis may occur anywhere within the circulatory system, however it can be especially life threatening when this occurs in the lower body, heart, lungs or brain resulting in deep vein thrombosis, acute myocardial infarction, pulmonary embolism and acute isechemic stroke.

Two pathways or coagulation cascades lead to the formation of a clot, known as the intrinsic and extrinsic pathways. These two pathways are initiated by distinct mechanisms but converge along a common pathway. Clot formation in response to an abnormal vessel wall in the absence of tissue injury is the result of the intrinsic pathway and clot formation in response to tissue injury is the result of the extrinsic pathway. The coagulation cascades are very complex and involve a number of different proteins known as clotting factors.

People who suffer from cardiac or vascular diseases and patients that have undergone surgical procedures are at risk of developing blood clots that may result in life-threatening clinical conditions. Such people are often treated with blood-thinning or anticoagulant drugs. However, the amount of anticoagulant in the bloodstream must be maintained at the proper level; too little may result in unwanted clotting whilst too much can result in haemorrhaging. As a result routine coagulation screening tests have been developed in order to evaluate the coagulation status of blood or plasma.

A useful measure of coagulation is the so called prothrombin time (PT) test. The PT test was first developed in 1935 and measures the tissue factor-induced coagulation time of blood or plasma. This can provide an assessment of the extrinsic coagulation pathway and is sensitive to factors I, II, V, VII and X. The test is performed by adding a clotting agent such as thromboplastin and Ca2+ to a patient sample and measuring the time for clot formation. Portable coagulation monitors such as the CoaguChek® Plus coagulation meter have been developed which measure prothrombin time using non-anticoagulated capillary whole blood from a fingerstick or lancing device. Such monitors have been shown to be a valuable tool for patients on long-term oral anti-coagulation therapy.

However, the traditional expression of PT test results is inadequate for international comparison because the values depend upon the nature of the thromboplastin used. This has lead to the adoption of the Internationalised Normalised Ratio or INR as a way of expressing prothrombin time, where:

$$INR=(PT\ \text{ratio})^{ISI}$$

where ISI is the International Sensitivity Index and $$PT\ \text{ratio}=\text{Patient's } PT/\text{Mean Normal } PT$$

The ISI is derived from the calibration line of the value of PT for a number of samples, obtained using a particular thromboplastin versus the World Health Organisation (WHO) international reference preparation for thromboplastin (human combined 67/40). A particular value of ISI, which takes into account the particular method and type of thromboplastin used, is assigned to each PT system, whereby each PT ratio can be translated into a standardized ratio. By employing INR, patients should be able to maintain a satisfactory level of coagulation which is independent of the PT system used.

Another method of measurement of coagulation in either blood or plasma is the Activated Partial Thromboplastin Time Test (APTT). This test is a measure of the time of coagulation that occurs when the intrinsic pathway is activated. This is achieved by the addition of an activator (kaolin) to the sample in the presence of calcium ions and phospholipid (partial thromboplastin). APTT is used to evaluate the intrinsic coagulation pathway which includes the factors I, II, V, VIII, IX, X, XI and XII. Formation of complexes on the surface of the phospholipid enables prothrombin to be converted into thrombin, which results in clot formation.

APTT is used as a routine test for monitoring heparin therapy during surgical procedures, as a preoperative screening test for bleeding tendencies and to assess the overall competence of the patient's coagulation system. This test is commonly carried out in the central laboratory.

Activated Clotting Time Test (ACT)

This test resembles the APTT test and is used to monitor a patient's coagulation status during procedures that involve the dosing of high amounts of heparin, such as percutaneous transluminal coronary angioplasty (PCTA) and cardiopulmonary bypass surgery. The ACT test is considered as one of the best laboratory tests for the control of heparin therapy, both for patients undergoing treatment for thromboembolic disease and for those on extra-corporeal circulation. For those patients taking heparin, prolongation of the ACT is directly proportional to the concentration of heparin in blood. Monotoring is important and underdosing or overdosing of heparin may result respectively in pathological thrombus formation or serious hemorrhagic conditions.

The original ACT test utilized a glass tube with a celite activator and it was necessary to invert the blood tube every 15–30 seconds so as to continually reexpose the blood sample to large amounts of glass. The MAX-ACT™ test has been developed by Helena Laboratories which overcomes the need to invert the tube yet at the same time providing a large exposure to glass by the use of additional glass beads.

Thrombin Time Test (TT)

This test measures the rate of formation of a fibrin clot in plasma by the action of thrombin on fibrinogen, compared to a normal plasma control. The test is performed by adding a standard amount of thrombin to a patient's plasma that has been deprived of platelets and measuring the time for a clot to form. It has been used in the diagnosis of disseminated intravascular coagulation and liver disease and is generally performed in the central laboratory.

Other Tests

Clotting assays have been developed which target specific factors such as factor VIIIa that is indicative of factor IX deficiency. Another example is an assay for factor VIII, which constitutes a test for haemophilia. Other tests include assays to measure the levels of activation peptide factor IXa, antithrombin, protein C and protein S.

Immunochemical assays have also been developed to identify and measure the various markers of coagulation and thrombosis.

Various instruments have developed for use in the laboratory and as POC. In addition to this, devices have been developed which allow the patients to home-monitor their blood coagulation. This is especially useful for patients who are on long-term anticoagulation therapy, such as warfarin.

Various techniques are employed to measure blood coagulation, as exemplified below.

U.S. Pat. No. 5,534,226 assigned to International Technidyne Corporation, discloses an apparatus and method for performing a coagulation time test on a blood sample whereby the blood is deposited into a capillary via a reservoir disposed within a disposable cuvette. The sample is then caused to reciprocally move within the capillary and blood forced to transverse a restricted region. Coagulation is determined to have occurred when the time required to transverse the restricted region is a predetermined percentage longer than the previous time.

U.S. Pat. No. 6,060,323 assigned to Hemosense, discloses a single use electronic device and test card for the measurement of the coagulation or lysis of a blood sample. The sample is caused to contact two electrodes, which measure the change in impedance corresponding to the change of viscosity of the sample as it clots.

U.S. Pat. No. 4,849,340, assigned to Cardiovascular Diagnostics, discloses an optical detection method for the determination of prothrombin time whereby capillary action is used to draw a predetermined volume of a liquid sample into a reaction chamber. Magnetic particles are caused to mix with the sample in a reaction chamber that are then agitated by an oscillating magnetic field. Light is shone onto the sample and subsequently detected. The point of coagulation is determined from the change in degree of the magnetic particle movement.

WO96/00390 discloses a fully disposable single-use device for determining blood-clotting activity whereby the distance traveled by the sample along a porous substrate is indicative of the clotting time.

U.S. Pat. 5, 039,617 assigned to Biotrack, describes a method and capillary flow device for carrying out measurement of Activated Partial Prothrombin Time (APTT) analysis on a capillary blood sample. The clotting time is measured by the cessation of blood flow in the capillary. The flow rate may be determined by flow or pressure sensors. The width of the capillary can vary from 0.05–3 mm and requires a sample volume of no more than 40 ul. Alternatively, if the sample contains particles, flow can be detected by observation of the speckle pattern resulting from the interaction of a light source, e.g. LED or laser, with the agitated particles in the capillary track.

The relationship between the changing impedance of a clotting blood sample has been studied (American Journal of Clinical Pathology 67:470–476, 1977). Measurement of the impedance of a blood sample over time was made, the resulting impedance curve representing the various processes in involved during clotting.

Measurement of Platelet Aggregation

Platelets are colourless cell fragments of about 2–4 um in diamter and are present in blood. Normal platelet counts range from 180,000–400,000/uL, however a platelet count of 50,000/uL is suffice for normal hemostasis. After vascular damage, for example after surgery, higher platelet counts are needed, sometimes in excess of 100,000/uL. The purpose of platelets is to repair gaps in the blood vessel wall by either adhering to themselves or to damaged tissue. When cells become damaged, they release certain chemicals which cause the platelets to change from a discoid to a spherical form and become sticky, known as the the aggregation-adhesion reaction. Platelets are thought to play an important role in the pathogenesis of isechemic heart disease; acute myocardial infarctions and unstable angina are clinical conditions associated with increased concentrations of certain platelet factors. Furthermore platelet dysfunction is one o the several major causes of bleeding after cardiopulmonary bypass. Platelets are also thought to contribute to the long-term process of atherogenesis by the release of growth factors and platelet function may also be influenced by high and low density lipoproteins. Thus screening for platelet function is an important and common hematological test.

Traditionally, this measurement was carried out on samples of platelet rich and platelet poor plasma, denoted respectively as PRP and PPP, using a Born aggregometer which measures the transmission of light through the sample.

U.S. Pat. No. 4,319,194 discloses an aggregometer which is able to carry out platelet analysis on whole blood. Wire shaped electrodes are inserted into the blood sample to which an aggregating agent is added and the change in impedance is recorded as a function of time. However movement in the wires causes variability in the interelectrode dictance and in the impedance measurements.

U.S. Pat. No. 6,004,818 asigned to Chrono-Log Corporation, discloses a method to measure platelet aggregation whereby the sample is caused to flow between adjacent parallel surfaces of electrode tips which define a channel. The electrodes are placed into a cuvette filled with the blood sample along with a means for stirring the sample.

DISCLOSURE OF THE INVENTION

It is an object of the invention to provide a simple and inexpensive apparatus and method which is capable of measuring clotting times on a whole blood or plasma sample (herein defined as sample fluid).

An aspect of the invention provides for a disposable test-device containing at least one microchannel which is capable of being inserted into a meter for the determination of the clotting time of a sample fluid.

A further aspect of the invention provides for an integrated penetration device and microchannel such that the microchannel is in fluid connection with the penetrating means.

A further aspect of the present invention provides a device for measuring the clotting time of a sample fluid within a microchannel as defined herein, and means for determining in use when or where flow of said fluid along said microchannel has stopped, by the use of electrodes situated along the inner and/or outer surface of the microchannel.

A further aspect of the invention provides a method and device for measurement of the clotting time of a sample fluid whereby a sample is caused to flow into a microchannel, whereby the change of impedance of the fluid is monitored as a function of time.

The invention provides a disposable test-device comprising a support member upon or within which is provided at least one microchannel. The purpose of the microchannel is to receive and accommodate the fluid sample. A sample received by the microchannel mixes with clotting activation factors present within the channel, preferably coated on the inner surface of the microchannel and/or the sample collection reservoir. The sample will then flow by capillary action along the length of the channel until it ceases to flow or flow will have been determined to be less than a certain threshold. The distance travelled will then be indirectly determined by measurement of the capacitance or impedance between electrodes situated either within or outside of the channel. Vents are provided at any suitable place along the microchannel to enable the sample to flow, thus displacing the air or gases contained within.

A reservoir may be provided in fluid communication with said one or more microchannels such that the fluid sample may be easily collected. Alternatively the sample may be transferred directly to the microchannel via an inlet port.

The microchannels of the present invention may be of a constant diameter or may be of a varying diameter along its length. The flow rate along the length of the capillary decreases as the channel fills due to the increasing area of surface contact between the sample and the walls resulting in increased friction. A way of achieving constant flow rate in a capillary tube is to increase the diameter as a function of the capillary length, as disclosed in U.S. Pat. No. 4,756,884.

However, for some measurements, the reduction in flow rate with length may be considered advantageous. Typically, measurement of APTT requires a time of up to 500 seconds to elapse before coagulation is deemed to have taken place. A long channel length would be required for flow to be maintained over such a long period of time and thus any decrease in flow rate would serve to decrease the total sample volume necessary.

A reservoir of a larger volume than the microchannel may be provided in fluid connection with the microchannel. The purpose of such a chamber is to intially collect the sample. During use, the sample is applied to the inlet port where it is drawn into the chamber. If, for example, the sample was capillary blood obtained from lancing the finger, the user would then be able to remove the finger after the chamber had filled to an appropriate amount. The sample would then enter and move along the smaller diameter capillary channel. Coagulation promoting factors such as thromboplastin could be coated on the inner walls of the chamber or alternatively on the walls of the capillary.

As mentioned above, one or more vents are provided to allow for fluid flow along the capillary. Vents may be used to control fluid flow. For example, a first vent could be situated to allow ingress of fluid into the chamber but not into the subsequent capillary channel. A second vent could then be opened, to allow the passage of fluid along the microchannel. Alternatively, flow of fluid may be controlled by the use of other flow controlling means. Any suitable flow control method may be employed with corresponding means to affect such a control method. For example Piezo-electric pumping, electrokinetic or mechanical methods such as 'unblocking' the flow along a selected conduit, —e.g. by allowing a gas bubble to escape or by opening a valve. In certain embodiments the flow control means comprises a hydrophobic gate situated within the conduit/microchannel. A hydrophobic gate as herein disclosed refers to a hydrophobic surface region within a hydrophilic channel such that the flow of fluid is interrupted. By changing the hydrophobic nature of the gate, ie by making the hydrophobic region more hydrophilic, fluid may then be allowed to flow along the channel. Hydrophobic gates may be used to control the flow of fluid within a single microchannel or may be used to switch or redirect flow from one microchannel to another.

Alternatively, the hydrophobic nature of the gate may be maintained as it is and a increased pumping force (e.g. provided by a mechanical or electro-osmotic pump) may be applied in order for the fluid to breach the hydrophobic gate.

Electrodes which provide the basis for the measurement of the electrical properties of the sample are provided along the length of the microchannel and may run along its entire length or along a portion of its length. The electrodes are also in electrical contact with contact points on the support member. The strip is designed to be inserted into a meter such that contact points on the support member engage with and make electrical contact with corresponding contact points in the meter. Electrical parameters measured by the electrodes are then transmitted to the meter which is able interprete the signal in order to give a result. The meter will also have stored calibration information such that a value of INR may be given.

The electrodes may be of any suitable inert conductor and may be selected from amongst others, carbon, gold or platinum. The electrodes run along either the entire length of the microchannel or a portion thereof. The electrodes may be produced by the printing of an ink onto the microchannel or by another means of deposition, for example vacuum or sputtering. The electrodes may run along either the outside or the inside of the channels. One advantage of the electrodes being situated on the outside of the microchannel is that the electrodes, which may interfere with the coagulation process both by virtue of its physical shape and chemical composition, do not come into contact with the sample. Furthermore, carbon is able to adsorb species in blood thus affecting the surface chemistry.

The electrodes may be any suitable shape and size and would typically be present as a line or thin band whose width might be anywhere between 1–99% of the circumference of the channel. The electrodes would be situated typically on opposing sides of the channel and would not neccsarily be of the same width. As disclosed above, the electrodes could cover substantially all of the inner or outer surface area or just a small section. According to one embodiment, electrodes are provided on opposing sides of a fluid channel by forming a first channel which is filled with a conductive material, and forming a second channel for conveying the test fluid, the second channel cutting across the first thereby thereby forming two conductive portions within respective opposite sides of the second channel. Furthermore, where the device has flow control means operating via electro-osmotic force, the driving electrodes are preferably positioned in close proximity to one another. This allows high electric fields to be achieved without applying unnecessarily high voltages.

The conductive portions formed in accordance with the invention could be utilised for an electrochemical sensor arrangement. Micromachining techniques for making the abovementioned intersecting channels are preferred since they can be used to fabricate microchannels which can be formed close to one another, permitting dense arrays thereof.

As used herein the term "microchannel" refers to a channel, of any suitable cross-section, whose smallest lateral dimension is less than approximately 500 µm. In the microchannels of the preferred embodiments of the invention this dimension is preferably less than 200 µm, most preferably between approximately 10–200 µm. The length of the channel may be any depending upon the specific test. However, it is likely that the length of the channel will be between 1–10 cm giving a volume of between 200 nl –2 ul. For example, the total volume of a 30 cm channel having a diameter of 40 um would be approx 19 ul.

Such microchannels are beneficial for a number of reasons in the context of an analyte sensing device. The volume of fluid required to carry out an assay is correspondingly small. In the context of the measurement of a bodily fluid a small sample volume is beneficial since it means that it is easier to provide a sufficient volume for a valid test. This test is designed to be carried out using a whole blood sample obtained from a capillary, for example a fingerstick or other suitable lancing point. A reduction in sample volume also corresponds to a reduction in pain since a smaller needle can be used to lance the skin.

It will be appreciated that by incorporating a microchannel into such a measurement device, accurate determination of the time taken to clot can be achieved since even for samples exhibiting poor clot formation, the relatively small lateral dimensions of the microchannels defined herein mean that even a small amount of clotting should arrest the flow of fluid therein. Furthermore a microchannel will require less sample volume overall and can be coiled or otherwise fitted onto a reasonable surface area without having to compromise its length. Maximising the length of the channel is important in order to accommodate long clotting times—e.g. 20–30 seconds for blood for the measurement of PT and to give greater measurement resolution.

The means for determining when flow has stopped may done directly e.g. it may comprise a flow rate sensor, preferably one which senses such flow rate electronically. Clearly when the sensed flow rate is zero or at least below a threshold, flow is determined as having stopped.

The flow rate is measured by the rate of change in impedance between two electrodes across the channel. The electrodes can preferably be formed as described earlier. The resistive part of the impedance may be measured. For example an array of electrodes may be spaced along the channel to provide an incremental signal depending upon how far the blood sample has travelled. Alternatively a single large electrode might be provided along a wall of the channel, the resistance between it and a counter electrode depending upon the degree with which the larger electrode is covered.

Preferably the purely capacitive component of the impedance is measured. This means that the electrodes need not be in contact with the sample fluid. Again a series of spaced electrodes could give a discrete reading or, preferably, a single pair of elongate electrodes could be formed—e.g. on opposing walls of the channel. It will be recognised that the capacitance between the two 'plates' will depend upon the extent to which the channel is filled with blood as a result the difference in relative permittivities (dielectric constants) of air and blood.

With optical sensing techniques, difficulties arise when measuring across a narrow capillary due to the very short path length, the latter being dependant upon the strength of the optical signal. Alternatively, shining light parallel to the channel requires accurate alignment of the optics as well as the use of mirrors. Furthermore, during the clotting process, it is the leading edge of the sample that has a tendancy to clot first. Thus light directed parallel to the channel will pass through both unclotted and clotted blood, making the measurement more complicated. In addition, the optical signal produced, for example, as a result of a speckle pattern, is complicated, and requires a complex algorithm to evaluate the results. Optics are also expensive, requiring both a light source and a detector and the question remains of where to place them in order to observe the clotting process. With respect to the present invention no such difficulties arise with regard to placement of the detection system since the electrodes run along the channel. Since the impedance measured is indirectly proportional to the diameter of the microchannel, very small diameters are actually advantageous from this point of view. The electrodes are situated along the length of the channel and therefore the impedance measured by the electrodes is a cumulative measurement, dependant upon the length or volume covered by the sample. Thus the question of where to place the electrodes in order to monitor the clotting process is not such a critical issue. Furthermore, the detection system based upon this method is far easier and cheaper to manufacture than an optical system.

Insert

The capacitance of a parallel plate capacitor is given as follows $$C = \epsilon_o \epsilon_r A/d$$

where:
$\epsilon_o$=permittivity of free space
$\epsilon_r$=relative permittivity of the dielectric between the plates
A=surface area of the plates
d=distance between the plates Assuming that the electrodes have a constant width w and length l, this becomes $$C = \epsilon_o \epsilon_r wl/d$$

Now if the channel is partially filled to a distance x with blood having a relative permittivity $\epsilon_1$ and the rest of the channel is empty, having a relative permittivity, $\epsilon_2$ the two adjacent sections of the channel may be considered as separate capacitors. The capacitance of the filled portion is $$C_{filled} = \epsilon_o \epsilon_1 wx/d$$

The capacitance of the empty portion is $$C_{empty} = \epsilon_o \epsilon_2 w(l-x)/d$$

Since these two capacitances are electrically in parallel, the combined capacitance is equal to their sum, i.e.:

$$C = \epsilon_o \epsilon_1 wx/d + \epsilon_o \epsilon_2 w(l-x)/d$$

$$= \epsilon_o w/d (\epsilon_1 x + \epsilon_2 l - \epsilon_2 x)$$

By measuring the total capacitance, C and by knowing the other constants, the distance x, travelled by the blood may be calculated:

$$C = = \epsilon_o w/d (\epsilon_2 l + x(\epsilon_1 - \epsilon_2))$$

$$dC/\epsilon_o w = (\epsilon_2 l + x(\epsilon_1 - \epsilon_2))$$

$$x = 1/(\epsilon_1 - \epsilon_2)(dC/\epsilon_o w - \epsilon_2 l)$$

It will be seen from the above that as well as being able to monitor the rate of change of capacitance in order to determine the time taken for flow to stop, it is possible to measure the value, x, of the distance travelled by the blood before clotting. This gives a relative measure of the prothrombin time since the longer the blood takes to clot, the further along the channel it will progress.

This can therefore be used, for example, as a cross check on the direct time measurement.

It will further be seen from the above equations that the capacitance, and in particular the change in capacitance achieved by introducing blood between the plates, is also inversely proportional to the distance between them, d. Thus it will be seen that a higher absolute change in the value of the capacitance, C may be achieved by having a channel whose cross-sectional dimensions are significantly smaller in the direction normal to the pates than in the direction parallel to them. Whilst giving a large capacitance change however, this might be inconsistent with the need for rapid arresting of flow on clot formation. Thus in an alternative embodiment a parallel array of microchannels is provided, each with a pair of electrodes, and the cumulative change in capacitance is measured. This can give an equally large change but without prejudicing the propensity of the flow to be arrested by a clot forming. As well as the above application there are many other envisaged applications for a microchannel with electrodes therein and thus from a further broad aspect the present invention provides a device comprising a microchannel and a pair of electrodes therein. In yet another embodiment, an array of microchannels may be provided, each of differing diameters. The channels or single channel may be of a constant diameter, or vary along its length. For example, the diameter of the channel may be varied to speed up or slow down the flow of sample, thus enabling it to efficiently solubilize the coagulation promoting chemicals situated on the surface of the channels. There may be provided as surface coatings, different coagulation promoting chemicals within different tubes so for example measurement of PT and APTT might be carried out simultaneously.

The microchannel itself will be fabricated from materials having the appropriate physical characteristics. The microchannel should possess good thermal conductivity, smooth capillary flow, allow for a uniform coating of reagents, as well as itself not promoting the coagulation process. The material should also assure that once blood clotting has taken place, flow should stop or slow down. Studies have shown for example, that contact with borosilicate or commercial siliconized borosilicate markedly shortens the PT. The use of such materials is therefore avoided. The channels may also be coated with a capillary retarding or promoting agent if necessary.

In an alternative embodiment, the microchannel may be designed such that the sample flows into the microchannel, filling the channel to a predetermined depth, whereupon flow in the lateral direction stops. Electrodes in this case may be provided on the inner or outer surface of the channel, the electrodes running along either an entire portion or along a section of the channel. Again, the coagulation process can be observed by measurement of the change of impedance with respect to time. By measurement and subsequent analysis of the impedance curve, one is able to determine the onset of coagulation.

Microchannels in accordance with the present invention may be fabricated using any suitable technique. In particular, where provided, the microchannels may be made using any suitable micro-fabrication technique such as embossing, plasma etching or laser photo-ablation. As for the material of the microchannel it may be fabricated from any suitable microfabricated plastic such as polyester, polycarbonate, polystyrene or polyimide. Preferred polymers are polycarbonates. These allow a subsequent laser finishing to generate a secondary micro- or nano-structure (e.g., any desired patterns or other finishing can be formed in the microchannel). Polystyrene shows preferable characteristics in the lamination process. Thus polycarbonate could be used as the lower laminate and polystyrene used as the upper. Normal lamination processes use foils coated with a pressure sensitive or hot melt adhesive to join a foil to a substrate or another foil. Such a standard process may present problems in conjunction with the described device. First, foil is needed which is suitable for the printing process. This is difficult with any pressure sensitive adhesive due to problems within the printing equipment. Such problems can be addressed with a foil coated with a hot melt adhesive, where the adhesive becomes tacky only at an elevated temperature (e.g. 80° C.). The deposition of ink to print the electrodes and other structures is quite easy with this system but it can present problems during the lamination step. The glue layer becomes substantially liquid at elevated temperatures with the consequence that the printed structure looses shape and gets stretched and deformed. Such deformation is not only a cosmetic problem for an electrode, it changes the electrode surface (which is directly proportional to the response signal) as well as the internal resistance of the material and the electro-catalytic properties.

Apart form the foregoing problems, there is the additional problem of glue entering and clogging or misshaping the channel. For the chip described above, the most advantageous process is an adhesive-free thermal bonding process of the preprinted foil to the chip base plate. The bonding happens at an elevated temperature with a stamping tool or a hot roller press. The temperature is close to the glass transition temperature ($T_g$) of the polymer thus the low molecular weight portion of the polymer will become mobile and tacky while the high molecular weight portion of the polymer still supports the integrity of the foil or film. The low molecular weight portion of the polymer will bond both pieces (base plate and foil with electrodes) together, additionally it will follow the shape of the printed electrodes, which can be between 5 and 30 $\mu$m thick. Therefore, one does not see a leakage between base plates and printed areas. Ideal bonding is achieved with the same thermoplastic polymers such as polystyrene on polystyrene or polycarbonate on polycarbonate. However, with the right regime and temperature/pressure combination polycarbonate can be bonded on polystyrene as well. But duro-plastic (non thermoplastic) materials are not suitable for such a process.

The material is chosen on the basis of the suitability of various parameters such as its microfabricability, its inertness to the coagulation process, the degree of hydrophilicity, ability to form smooth channels, its thermal capacity and conductance, ability to carry an electrode on its surface, robustness and so on. If desired the material may have additionally a surface coating to influence the degree of hydrophilicity and therefore the degree of capillarity. This will in turn determine the rate of flow of the blood sample.

Measuring devices in accordance with the present invention may be fabricated using any suitable technique. In particular, where provided, the microchannels may be made using any suitable micro-fabrication technique such as but not limited to embossing, plasma etching or injection moulding One or more electrodes may be formed on a second substrate which is then laminated to the main support member of the device. Methods used to deposit the electrodes onto the substrates may be chosen preferably from a printing method, more preferably a screen-printing method. Alternatively, chemical or physical vapour deposition techniques could be employed. Generally speaking, the electrodes according to all embodiments of the invention may be formed of any suitable inert material such as carbon, gold, platinum, etc. According to one embodiment, carbon electrodes, optionally coated with reagents are provided on the second substrate by screen-printing, which is then laminated onto the support member thus closing the channel or channels. This allows a very straightforward fabrication method for the embodiment in which electrodes are formed within a closed channel.

Lamination of one substrate to another will normally be carried out such that both laminates are perfectly aligned and that no further timming or cutting is necessary. However, the the device could be fabricated for example by firstly a lamination step followed by a cutting step whereby the second substrate may be trimmed to the shape of the support member. Lamination may be carried out by various methods such as ultrasonic or thermal welding or bonding, or by the use of an adhesive. Prior to laminating the upper substrate layer onto the support member, the walls of the microchannel and/or the reservoir may be coated with a layer of a coagulation promoting agent such as Thromborel R (trademark), a thromboplastin clotting agent available from DADE Behring.

The strip may additionally contain means for heating the support member, so that the blood or plasma may be heated to a predetermined temperature within the microchannel. This may be provided on the support member itself or on the outer surface of the microchannels. Such means could be in the form of additional electrodes in electrical contact with the meter, such that heat is generated by virtue of current flow from the meter to the electrodes. Alternatively, heating of the sample could be achieved by insertion of the strip into the meter, the heat being generated by the meter itself which would serve to warm up the sample by convection. In addition, temperature control means may be provided which serves to control the heating means either switching it off or on, or altering the rate of heating. In this way the sample may be kept at a constant temperature or within a certain temperature range. Provision of the heating means on the strip itself is preferable due to the fact that the sample may be heated more quickly and efficiently with greater control of the temperature possible. According to one embodiment, the measurement electrodes may also function as the heating electrodes.

The strip may also have means to detect when adequate sample has been applied and thus begin the measurement. Such fill-detection means could be situated within the fluid reservoir and could comprise two spaced electrodes, measurement between which would determine the fill-state of the reservoir. A control unit present in the meter would control operation of any flow control means and be able to indicate any malfunctioning of the device. Indication of a full reservoir as determined by the fill-detection electrodes would send a signal to the control unit which would then control any flow operating means to cause the sample to flow along the capillary.

The meter will be able to display the results of the test. In addition, the meter will have a memory capability, be able to download information as well as have information downloaded to it. The meter may also be equipped with an algorithm to indicate what action if necessary needs to be taken as a consequence of the result. The meter may be a wireless communication device which can download and receive information to a doctor or website. The meter will also have the ability to store and interpret personal information regarding the patient. The meter may also have the ability to read remotely information regarding the strips as well as being able to store batch calibration codes remotely, i.e. optical etc.

According to one embodiment, the support member is formed with an integral needle at one end and the second substrate is then laminated onto the support forming a channel and leaving the penetration member exposed. According to another embodiment the integrated skin penetration member is provided is open on one side. The penetration member is arranged so that upon insertion into skin, the skin itself effectively forms a wall of the member to that it can act like a hollow needle. Most preferably this is achieved by forming the penetration member with walls tapering away from the open side—e.g. a V shape. Thus when viewed from a further aspect the invention provides an apparatus for obtaining and measuring fluid, comprising a skin penetration member having at least one longitudinal side open, the other sides being arranged so as effectively to cause the penetrated skin to act as the remaining longitudinal side of the member when the penetration member is inserted into the skin.

When viewed from a yet further aspect the present invention provides a method of fabricating a device for measuring the concentration of an analyte in a fluid comprising providing a support member, forming an open channel on a surface of the support member and laminating a second layer onto said support member so as to close said channel. The invention also extends to a device fabricated using such a method.

The needle is preferably shaped to aid skin penetration. For example the tip region of the needle is preferably substantially conical. Furthermore it is preferred that the tip region has a reduced cross-section-preferably less than 0.2 mm in width, most preferably less than 0.05 mm in width.

Moreover the needle is preferably arranged to minimise the risk of blockage upon insertion into skin. For example the aperture of the needle may be provided on a side surface of the needle, rather than at the tip as is conventional. Preferably the aperture of the needle is recessed, thereby avoiding contact with the skin upon penetration and thus potential blocking and/or damage The needle preferably has a bore such that the sample fluid is drawn up by capillary action.

The device is suitable for the measurement of clotting times in blood or plasma. Whilst the device is suited to measurement of prothrombin time (PT), other clotting times that may be measured using this technique are activated partial prothrombin time (APTT), activated clotting time (ACT) and thrombin clotting test-time (TCT).

BRIEF DESCRIPTION OF THE DRAWINGS

Certain preferred embodiments of the invention will now be described, by way of example only, with reference to the accompanying drawings in which:

FIG. 4(*b*) shows an alternative embodiment of FIG. 2 whereby the channels are of differing cross-sectional dimensions;

DETAILED DESCRIPTION OF THE INVENTION

Figure 1:
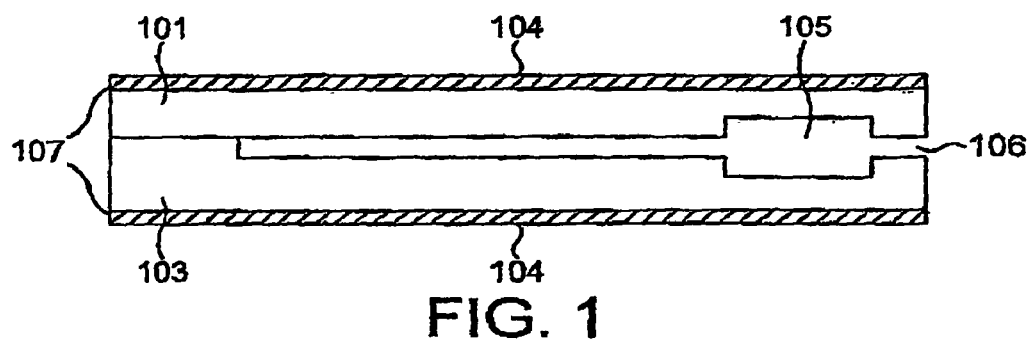
FIGS. 1 and 2 depict schematically a device suitable for measuring blood clotting.

As shown in FIG. 1, there is provided a disposable test-strip 100 comprising an upper and lower support 101 and 103. A microchannel 102 is formed into the upper surface of the lower support member 103. A upper support member 101 is laminated on top of the support member 103, thereby closing the open microchannel 102. Electrodes 104 are formed on the respective outer surfaces of the substrate layers and coplanar to the channel. The electrodes may run along the entire outer length to an edge of the device as shown in FIG. 1*a*, so that suitable electrical contact may be made between the leads and the meter (not shown).. The electrodes themselves may be covered by a further laminate in order to protect them. Also shown is a reservoir 105 into which the sample initially flows and a sample inlet port 106. As shown, the inlet port is substantially level with the microchannel and the sample reservoir fills by capillary action. However the sample inlet port may be situated above the device and the reservoir may fill by gravity. Alternatively the reservoir may be situated externally to the device such that it also functions as a sample collection device. The reservoir can be mounted onto the top surface of the strip and be formed by any conventional method such as injection moulding. Not shown in FIG. 1 are the vents to allow egress of air from the channel, heating or fill-detector electrodes or flow-control devices.

The flow control device may be positioned along the microchannel itself. The figures are for illustration purposes only and do not reflect the relative sizes of components within the device. Thus the reservoir will be of a certain volume relative to the microchannel such that it may store, an adequate volume of fluid in order to carry out the measurement. The reservoir is shown as being of a rectangular shape, however it may be of any suitable shape.

Figure 2:
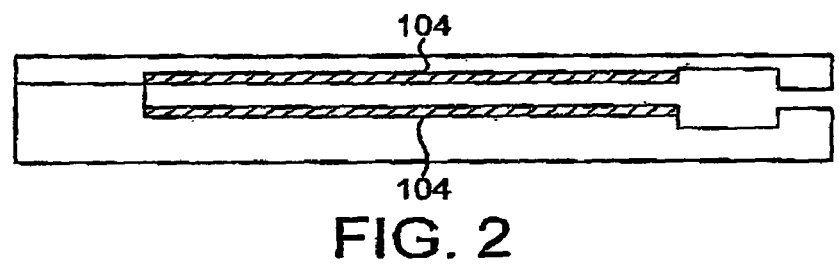

FIG. 2 shows another embodiment whereby the electrodes are situated on the inner surface of the laminates. Alternatively the electrodes may be present at spaced intervals along eithet the inside or outside of the channel. As an alternative to the electrode arrangement of FIGS. 1 and 2, both electrodes may be provided on either the upper or lower laminate.

Figure 3:
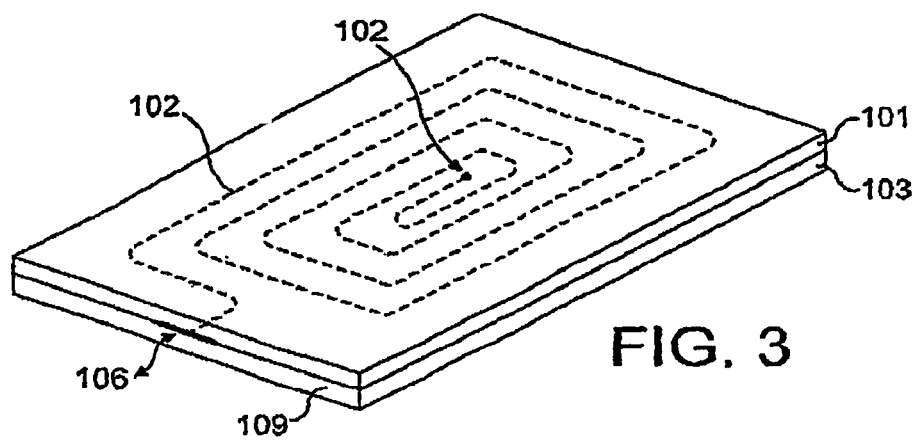
FIG. 3 depicts schematically a device suitable for measuring blood clotting with a spiral microchannel.

An alternative embodiment is shown schematically in FIG. 3. It will be seen that in this embodiment, the microchannel 202 is spiral shaped in order that an increased length can be achieved for a given surface area of the device.

It will further be appreciated by those skilled in the art that the capacitance between the two electrodes is proportional, inter alia, to the relative permittivity of the contents of the microchannel. The relative permittivity of blood is assumed to be approximately the same as that of water and alising is thus of the order of 80. On the other hand, the relative permittivity of air is approximately 1).

Accordingly, the overall capacitance between the two electrodes 104 will depend upon the proportion of the microchannel 102 which is filled with blood. An alternative estimate of the prothrombin time of the blood may therefore be obtained by measuring the value of the capacitance. This is calibrated empirically against the prothrombin times and is used to indicate an error requiring a repeat measurement if the two are not consistent.

Inlet port 106 in fluid connection to the microchannel is shown with regard to the spiral microchannel configuration and may be used for any configuration. The inlet port is designed such that a sample contacting the port is transferred into the microchannel. The front edge 109 is shown as being flat. It may however have a rounded shape or any other shape that it ergonomically advantageous. Alternatively, the sample may be applied to a reservoir in fluid communication with the microchannel.

Figure 4A:
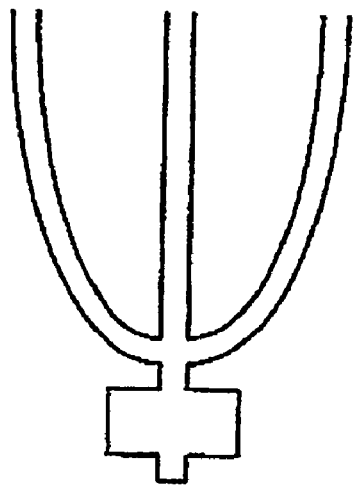
FIG. 4 (*a*) shows a strip according to the present invention comprising a plurality of channels.
Figure 4B:
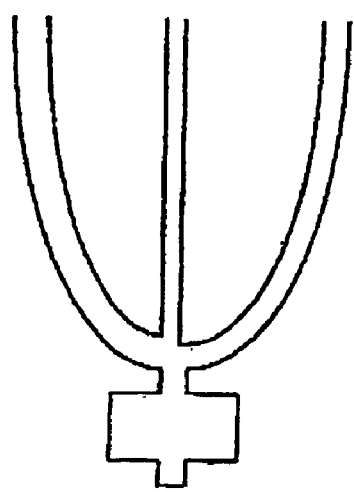

FIG. 4*a* shows an alternative embodiment comprising a plurality of channels. The channels have a common inlet port but are designed such that fluid does not pass from one to the other. FIG. 4*b* shows a plurality of channels of differing dimensions. By choosing differing dimensions, one is able to vary the ratio of cross-sectional area to the circumference of blood contacting the walls of the channel. In addition to having a plurality of channels of differing diameters, the channel or channels may have varying cross-sectional areas along their length.

Figure 5A:
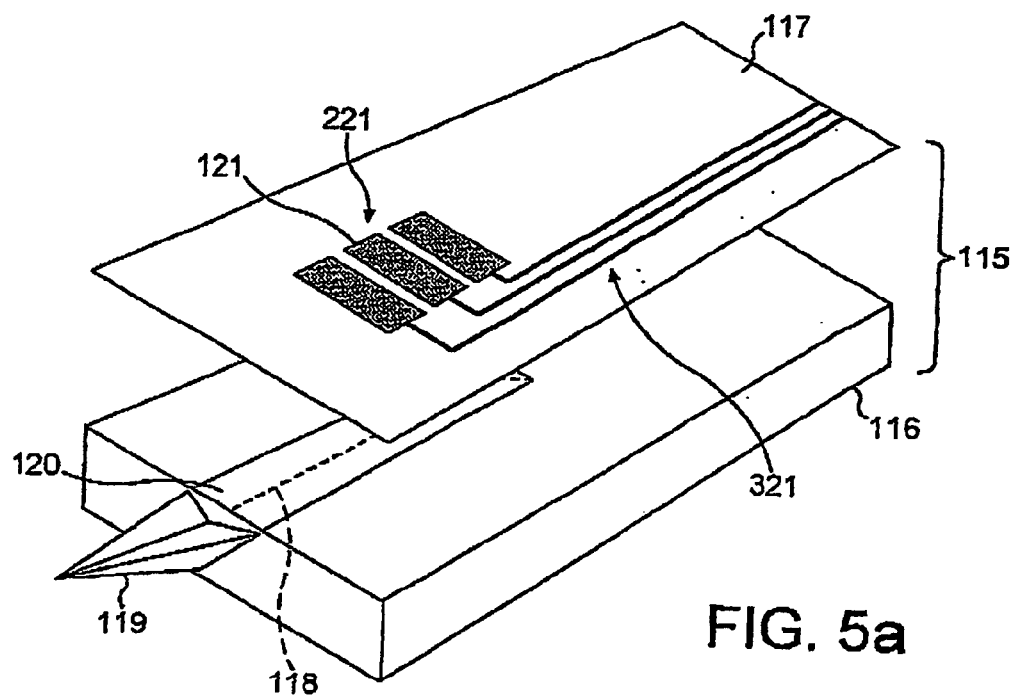
FIG. 5*a* shows an integrated penetration device and microchannel.
Figure 5B:
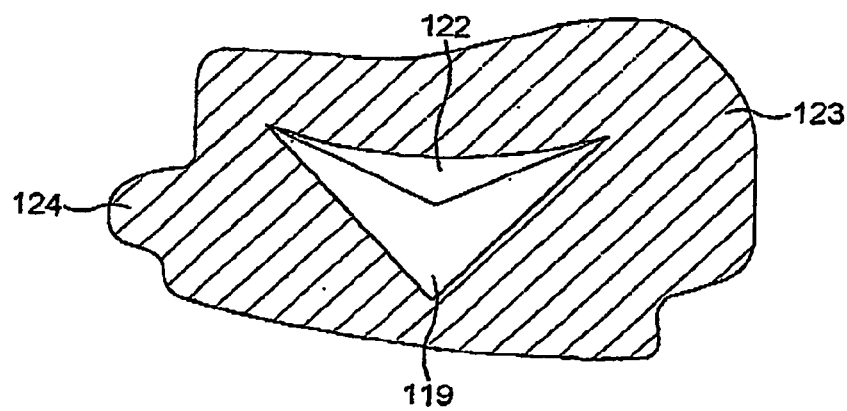
FIGS. 5*b–h* show further views of the penetration device.
Figure 5C:
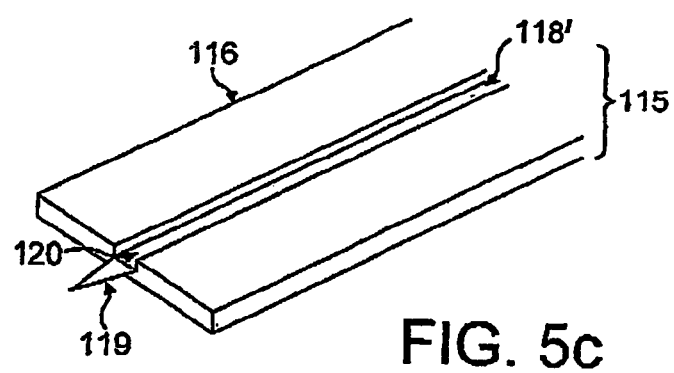

FIGS. 5*a–c* show two further embodiments of the invention which show an integrated penetration member and microchannel suitable for measuring the coagulation of a fluid. Considering the device 115 shown in FIG. 5*a*, it will be seen that it is made essentially of of a layer 116 onto which a second layer is attached or laminated (not shown). The lowermost substrate layer 116 comprises a moulded or stamped microchannel 118, as well as the integrally formed lance 119 arranged in close proximity with the entrance 103 of the microchannel. During manufacture, the microchannel 118 may be coated with suitable reagents, such as prothrombin, which can be applied by any conventional means, such as printing for example screen-printing or ink-jet printing, or spray coating during manufacture. The uppermost layer 117 is attached to the lower surface such that the measurement electrode is positioned on the underside of the formed channel. Alternatively the electrode may be positioned on the outer surface of the laminate 117. Not shown in FIGS. 5*a–c* is a reservoir for collection of the liquid, fill-detection electrodes, vents or heating electrodes . A vent or vents may be provided at any convenient location. Also not shown by FIG. 5*a* is the other electrode, between which measurement of the electrical parameter, ie impedance or capcitance is made. Electrical connection may be made between the ends of the electrode and suitable connection points situated within a test-meter. The upper layer 117 may be slightly longer than the lower one 116 to allow access to the tracks 321 for this purpose. According to this particular embodiment, electrodes are provided at spaced intervals along the upper laminate 117. Alternatively, one electrode provided substantially in parallel to the microchannel could be provided. Not shown in FIG. 5*a* is the "counter" electrode which may be provided at any suitable location on the lower or upper laminate 116,117 consistent with the earlier description, i.e. on the inner or outer surface of the microchannel.

It will be noticed in particular that the lance 119 of the strip 115 in FIG. 5*a* is essentially V shaped in cross section and tapers towards its tip. This means that when it is used to puncture a user's skin 123, as is shown in FIG. 5b, the two sides of the V force back a portion of the skin 123, forcing the epidermis to form the remaining wall 123 of an enclosed channel 124. Thus an open channel is effectively transformed into a closed one when it is inserted into skin. This allows fluid to be drawn up the channel 124 so formed and into the microchannel 118, without having to mould a very fine hollow needle. The microchannel 118 may also be formed with a V shaped profile for convenience of fabrication, but this is not essential as may be seen from the slightly modified embodiment of FIG. 5c and 5d in which the microchannel 118' has a rectangular profile.

In the use of the strip 115, the user first inserts the test-device into a meter.

Alternatively, the test-device may already be loaded either as a singular device or as a plurality of devices individually packaged within a cassette, into an integrated measurement and lancing device. The user then pierces their skin with the lance 119 and sample is made to flow, by means of capillary action, through channel 124 formed by the lance (119) and the skin 122, into the microchannel 118 preferably via a fill reservoir having fill-detection means to initiate flow of sample into the microchannel.

Figure 5D:
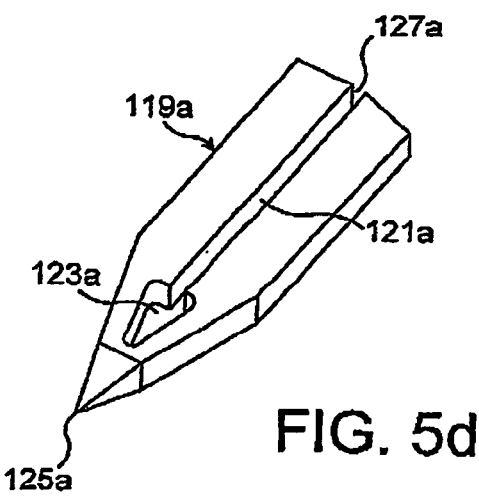

FIGS. 5d through 5g show alternative embodiments of lances for penetrating into a body-fluid laden layer of skin as an alternative to the embodiment of the lance 119 of FIGS. 8a and 8b. In FIG. 5d, the lance 119a is an integrally formed pointed protrusion from the device 115 (not shown in FIGS. 5d but identical to that in FIG. 5a) with a longitudinal capillary channel 121a cut completely through the thickness of the lance 119a. At a pointed distal tip 125a of the lance 119a, the lance 119a is provided with an enlarged area 123a of the channel 121a. The enlarged area 123a also is cut completely through the thickness of the lance 119a. At its proximal end 127a, the capillary channel connects with the microchannel 118 of the device 115 of FIG. 5a.

Figure 5E:
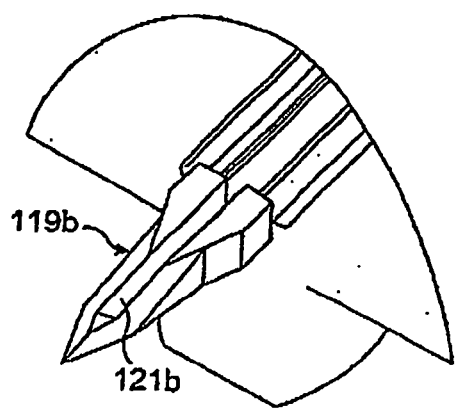
Figure 5F:
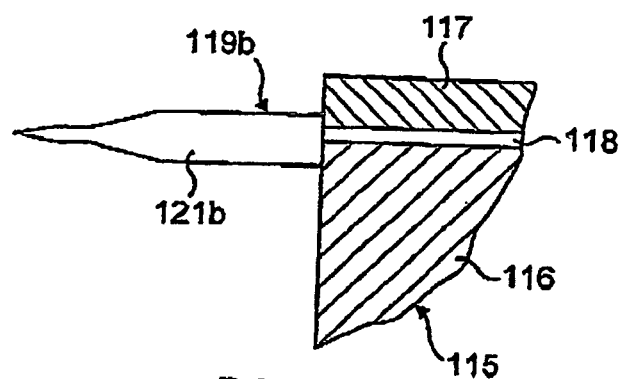
Figure 5G:
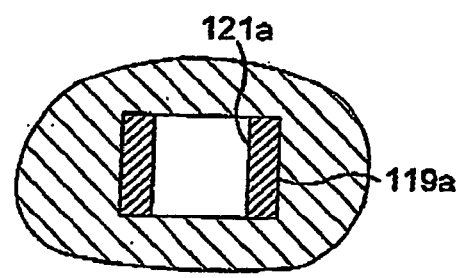

As shown best in FIG. 5g, the embodiment of FIG. 5d permits fluid to enter into the capillary channel 121a from opposite sides of the lance 119a and with the wall of the skin cooperating with the walls of the lance 119a to define an enclosed channel 121a. Fluid then can accumulate in the pooling area 123a and flow from the pooling area 123a into the capillary channel 121a as well as flow directly from the skin into the capillary channel 121a for passage to the microchannel 118.

In the embodiment of FIG. 5e, a lance 119b is of a design similar to that of FIG. 5d is shown but excluding the large pooling area 123a. Elimination of the pooling area 123a permits a narrower transverse dimension to the lance 119b. In addition to fabricating the device from molded parts, the base member 116 and lances 119, 119a, 119b can be stamped from electrically conductive material. In such cases, the base member may be an electrode. An electrically conductive base member and lance can be stamped from metal as described or formed in any other acceptable manner (e.g., photochemically etching a metal stock material, machining or other fabricating technique). While the electrically conductive base member can be made of stainless steel it can be also be plated with a second metal such as for example gold, platinum or silver or coated with a dielectric insulator.

Figure 5H:
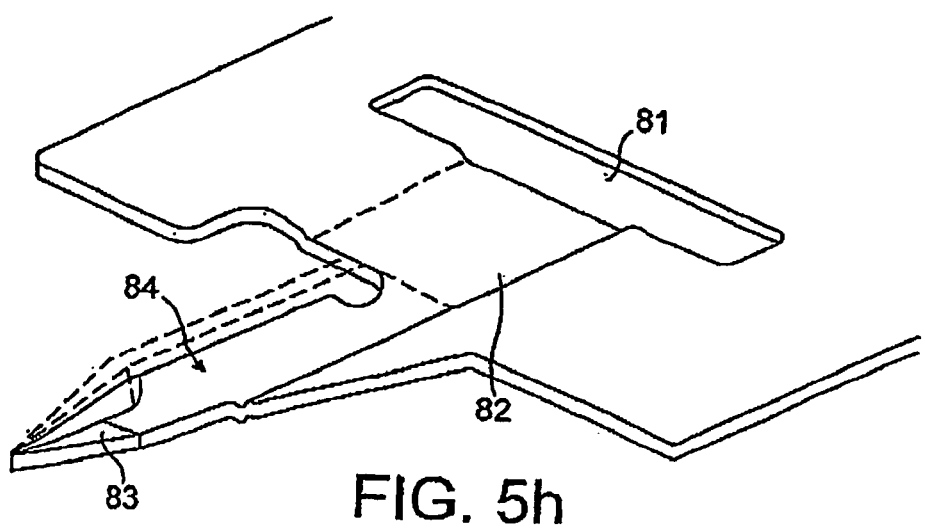

FIG. 5(h) shows an integrally formed base member and lance stamped from preferably one piece of sheet metal. The metal is preferably, but not limited to, stainless steel optionally coated with a noble metal such as gold or silver. Also shown on the base sheet is a microchannel onto which a second layer such as a test-strip could be attached. FIG. 5(h) also shows a stamped penetration member with a rectangular vent 81 which also serves as a capillary break ensuring that once fluid is taken up by the lance 83 into the sensing zone 82, the flow of fluid is halted. The vent may be of any suitable size or shape.

Figure 6A:
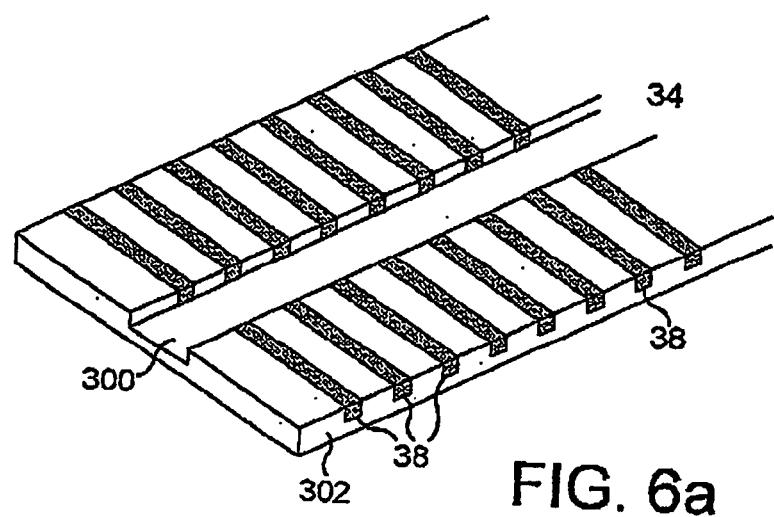
FIGS. 6*a* and 6*b* show an alternative configuration in which the microchannel is flanked by a series of longitudinally spaced pairs of electrodes.
Figure 6B:
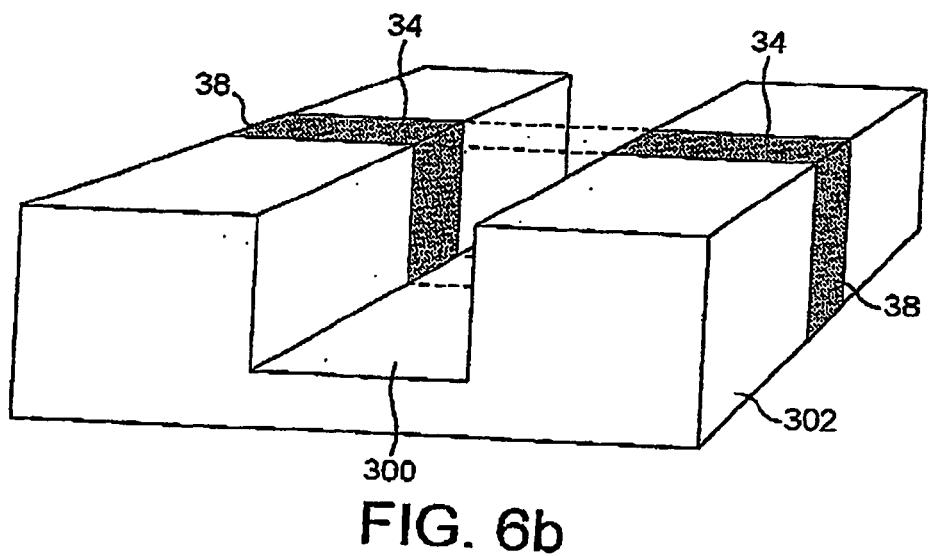

FIGS. 6a and 6b show an alternative configuration in which the microchannel 300 is flanked by a series of longitudinally spaced pairs of electrodes 38 integrally formed in the walls of the microchannel 300. In order to form these electrodes 38, firstly a series of parallel channels 34 is cut into the substrate material 302. The channels 34 are then filled with carbon to make them electrically conductive. The microchannel 300 is thereafter formed at right angles to the parallel channels 34 such that it intersects them. This creates the opposing electrodes 38 on each side of the microchannel 300.

This arrangement allows the progress of blood along the microchannel 300 to be monitored by measuring the electrical resistance between adjacent pairs of electrodes 38. As the blood reaches each successive pair, the resistance will fall from open-circuit, to a value of the order 200 kilohms. Thus a discrete reading for the distance travelled is obtained. This arrangement also demonstrates that the electrodes 38 may be allowed to come into contact with the blood. An inlet 206 in fluid communication with the microchannel is provided on an exterior surface of the support. A vent 207 is positioned at a far end of the microchannel such that air or other gases may be displaced from the channel allowing ingress of the sample. The vent may be positioned in any suitable place along the microchannel or the vent may be at the end 208 of the unsealed capillary. A set of metallic strips or wires 209 are positioned along either side of the microchannel and run along its length. These wires are themselves in electrical contact with a set of contacts 210 designed to be connected to the meter. These contacts may also serve to heat the sample or the microchannel prior to the sample insertion by passage of a current along the leads. Alternatively the strip may be heated by conductive strips within or on the support as shown in FIG. 1(b)

FIG. 1 (c) shows an alternative embodiment whereby microchannel 205 is positioned on the support 200.

As an alternative to the inlet 206, a reservoir may be provided for collection of the fluid sample As shown, in FIG. 3 the reservoir is positioned on the top side of the strip and designed to be in fluid connection with the microchannel.

According to a method of the invention, the test-strip is first inserted into the meter such that the contacts form an electrical connection with the corresponding contacts provided within the meter. A sample of blood is then applied to the end of the microchannel 102 which will then flow along the microchannel at which simultaneously a timer is started and the measurement commenced. Alternatively, a sample is drawn initially into a reservoir via the sample inlet port whereby fill-detector electrodes will determine whether enough sample has been applied. A flow controlling means will then allow the sample to be drawn into and along the microchannel under capillary action. The flow controlling means is activated by the fill-detection means such that the device requires no further input from the user. The fill-detection means could also serve to switch on the device. As the blood flows along the microchannel, its contact with the clotting agent causes it to clot. This eventually arrests the flow of blood part-way along the channel. The two electrodes 101 and 102 are connected to a measurement circuit (not shown) via connections 106 at the edge of the strip. This circuit is used to measure the capacitance between the two electrodes. This may be done in any way known in the art e.g. by including the device as part of an RC oscillator and measuring its frequency (which is inversely proportional to the capacitance). As the blood flows, the capacitance between the two electrodes 104 will change. A measurement is made when the flow of fluid has stopped or when the rate of change falls to within a predetermined value.

The actual prothrombin time measured is divided by a normalising factor, the time in which normal blood would clot taking into account the dimensions of the channel and the properties of the clotting agent. The result, in the form of an International Normalised Ration (INR) or value of prothrombin time would be displayed on a readout (not shown).

It will be appreciated by those skilled in the art that whilst some of the potential embodiments of the inventive concepts disclosed herein have been described in greater detail, there are many different variations and modifications to these possible. For example, devices in accordance with the invention may measure the clotting times of fluids other than those of blood.

What is claimed is:

1. A device for the measurement of clotting times of a fluid comprising an inlet port for the collection of the fluid sample and at least one microchannel with a lateral dimension of less than approximately 500 μm, the inlet port in fluid connection with the at least one microchannel, and at least two electrodes situated along the length of the microchannel, wherein the at least one microchannel is configured for the fluid sample to be transported therealong by capillary action and wherein the inlet port is an integrated penetration device for penetration into the skin of a user for collection of a capillary fluid sample.

2. A device according to claim 1 where the electrodes are of differing lengths and size dimensions.

3. A device according to claim 1 where the electrodes are situated on the inner surface of the microchannel.

4. A device according to claim 1 whereby the electrodes are situated on the outer surface of the microchannel.

5. A device according to claim 1 whereby an agent for the promotion of clotting of the fluid is situated on an inner surface of the device.

6. A device according to claim 1 comprising a reservoir in fluid connection with the microchannel for collection of the fluid sample.

7. A device according to claim 1 comprising a plurality of microchannels.

8. A device according to claim 7 whereby the microchannels are of different diameters.

9. A device according to claim 1 whereby the area of cross-section of the microchannel varies along its length.

10. A method of fabricating a device for the measurement of clotting times of a fluid comprising an inlet port for the collection of the fluid sample and at least one microchannel with a lateral dimension of less than approximately 500 μm, the inlet port in fluid connection with the at least a microchannel, and at least two electrodes situated along the length of the microchannel, wherein the at least one microchannel is configured for the fluid sample to be transported therealong by capillary action, the method comprising providing a first laminate, microfabricating said laminate to produce a michochannel, a fluid inlet port and optionally a fluid collection reservoir, providing an electrode along the length of the microchannel, providing a second laminate with an electrode provided on its surface and laminating said first and second laminates.

11. A method according to claim 10 where additionally flow controlling and fill detection means are provided on or within the device.

12. A method of measuring the clotting times of a fluid comprising introducing a capillary fluid sample into a microchannel with a lateral dimension of less than approximately 500 μm by capillary action via an inlet port that is integrated with the microchannel and that is a penetration device for penetration into the skin of a user for collection of a capillary fluid sample, whereby the total distance of flow of the fluid within a microchannel is determined by a measurement of the ratio of capacitance or impedance of the filled to the unfilled portion of the channel.

13. A method of measurement the clotting times of a fluid comprising introducing a capillary fluid sample into a microchannel with a lateral dimension of less than approximately 500 μm by capillary action via an inlet port that is integrated with the microchannel and that is a penetration device for penetration into the skin of a user for collection of a capillary fluid sample, whereby the speed of flow of fluid within the microchannel is determined by measuring the rate of change of capacitance or impedance.

14. A method of measuring the clotting times of a fluid comprising introducing a capillary fluid sample unto a microchannel with a lateral dimension of less than approximately 500 μm by capillary action via an inlet port that is integrated with the microchannel and that is a penetration device for penetration into the skin of a user for collection of a capillary fluid sample, whereby the coagulative state of the fluid within the microchannel is determined by measuring the rate of change of capacitance or impedance of the fluid.

* * * * *